United States Patent [19]
Harris et al.

[11] Patent Number: 5,043,415
[45] Date of Patent: Aug. 27, 1991

[54] NITROGEN-CONTAINING OXACALIXARENE AND CALIXARENE DERIVATIVES, POLYMERS INCLUDING GROUPS RELATED TO SUCH DERIVATIVES, AND USE OF SUCH COMPOUNDS

[75] Inventors: Stephen J. Harris; Maureen G. MacManus, both of Dublin; John Guthrie, County Kildare, all of Ireland

[73] Assignee: Loctite (Ireland) Ltd., Tallaght, Ireland

[21] Appl. No.: 248,874

[22] Filed: Sep. 23, 1988

Related U.S. Application Data

[63] Continuation-in-part of Ser. No. 20,918, Mar. 2, 1987, Pat. No. 4,882,449, Ser. No. 145,993, Jan. 20, 1988, Pat. No. 4,855,461, and Ser. No. 100,494, Sep. 24, 1987, abandoned, which is a continuation-in-part of Ser. No. 870,677, Jun. 4, 1986, Pat. No. 4,699,966, which is a continuation-in-part of Ser. No. 717,251, Mar. 28, 1985, Pat. No. 4,642,362, said Ser. No. 20,918, is a continuation-in-part of Ser. No. 870,677, , and Ser. No. 825,012, Jan. 31, 1986, Pat. No. 4,695,615, which is a continuation-in-part of Ser. No. 145,993, , and Ser. No. 717,251.

[30] Foreign Application Priority Data

Sep. 24, 1987 [IE]  Ireland ................ 2574/87
Dec. 18, 1987 [IE]  Ireland ................ 3444/87

[51] Int. Cl.$^5$ ............ C08G 63/78; C08G 69/14; C07D 313/00; C07C 45/105
[52] U.S. Cl. ............................ 528/205; 528/59; 528/323; 528/392; 549/348; 549/354; 549/397; 568/325; 568/631; 568/632; 568/633
[58] Field of Search ............ 528/225, 373, 392, 59; 549/348, 354, 397; 568/325, 631, 632, 633

[56] References Cited

U.S. PATENT DOCUMENTS

| | | | |
|---|---|---|---|
| 4,642,362 | 2/1987 | Harris et al. | 556/419 |
| 4,695,615 | 9/1987 | Leonard et al. | 526/194 |
| 4,699,966 | 10/1987 | Harris et al. | 528/12 |
| 4,855,461 | 8/1989 | Harris et al. | 549/348 |
| 4,866,198 | 9/1989 | Harris | 560/61 |
| 4,882,449 | 11/1989 | Harris | 556/419 |
| 4,908,399 | 3/1990 | Harris et al. | 524/243 |

FOREIGN PATENT DOCUMENTS 0196895 10/1986 European Pat. Off. .
0262910 4/1988 European Pat. Off. .
62-265250 11/1987 Japan .

OTHER PUBLICATIONS

Levine, A. J., "Synthesis and Properties of p-amino calix[4]arenes", Diss. Abstr. Int. B, 45(2), 562 (1984), CA 101:151561p, p. 690 (1984).
A. Arduini et al., "p-t-Butylcalix[4]arene Tetra-acetamide: A New Strong Receptor for Alkali Cations [1]," J. Inclusion Phen. 6, pp. 119-134 (1988).
Gutsche, C. D., "The Calixarenes", Topics in Current Chemistry, vol. 123, pp. 1-47 (1984).
Gutsche, C. D., "Calixarenes," Acc. Chem. Res. 16, pp. 161-170 (1983).
Olmstead, et al., "Metallocalixarenes: Synthesis and X-Ray Crystal Structures of Titanium (IV), Iron (III), and Cobalt (II) Complexes of p-tert-butylcalix[4]arene," J. Amer. Chem. Soc. 107, pp. 8087-8091 (1985).

Primary Examiner—John Kight, III
Assistant Examiner—P. Hampton-Hightower
Attorney, Agent, or Firm—Edward K. Welch, II; Eugene F. Miller

[57] ABSTRACT

The application describes nitrogen-containing an oxacalixarene or calixarene derivative of formula I:

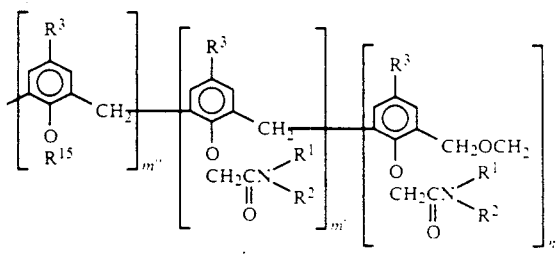

wherein
$m' + m'' = 0\text{-}8$
$n = 0\text{-}8$
$m' \geq \frac{1}{2}(m' + M'')$
$3 \leq m' + m'' + n \leq 8$
if $n = 0$, $m' + m'' \geq 4$
$R^3$ is H, halogen, or hydrocarbyl, aryl, hydrocarbylaryl or a substituted derivative thereof and $R^3$ may be the same or different on each aryl group;
$R^1$ and $R^{15}$ which may be the same or different are H or hydrocarbyl, aryl, hydrocarbylaryl or a substituted derivative thereof;
$R^2$ is selected from:
$R^4$ which is H, or hydrocarbyl, aryl, hydrocarbylaryl or a substituted derivative thereof,

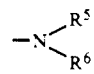

wherein $R^5$ and $R^6$ which may be the same or different are H, or hydrocarbyl, aryl, hydrocarbylaryl, or a substituted derivative thereof,
$-OR^1$, wherein $R^1$ is as defined above
and $R^{17}$ which is a residue of a hydrocarbyl, aryl, or hydrocarbylaryl group or of a substituted derivative thereof providing a bond to another oxacalixarene or calixarene derivative of formula I wherein $R^2$ is $R^{17}$.

The derivatives may be polymer-bound. Use of the derivatives for sequestration of metals is also described.

10 Claims, No Drawings

NITROGEN-CONTAINING OXACALIXARENE AND CALIXARENE DERIVATIVES, POLYMERS INCLUDING GROUPS RELATED TO SUCH DERIVATIVES, AND USE OF SUCH COMPOUNDS

This is a continuation-in-part of U.S. Ser. No. 020,918, filed Mar. 2, 1987, now U.S. Pat. No. 4,882,449, which is a continuation-in-part of U.S. Ser. No. 870,677, filed June 4, 1986, now U.S. Pat. No. 4,699,966, and a continuation-in-part of U.S. Ser. No. 825,012, filed Jan. 31, 1986, now U.S. Pat. No. 4,695,615, which is a continuation-in-part of U.S. Ser. No. 717,251, filed Mar. 28, 1985, now U.S. Pat. No. 4,642,362; and a continuation-in-part of U.S. Ser. No. 145,993, filed Jan. 20, 1988, now U.S. Pat. No. 4,855,461; and a continuation-in-part of U.S. patent application Ser. No. 100,494, filed Sept. 24, 1987, now abandoned, which is a continuation-in-part of U.S. Ser. No. 870,677, filed June 4, 1986, now U.S. Pat. No. 4,699,966, which is a continuation-in-part of U.S. Ser. No. 717,251, filed Mar. 28, 1985, now U.S. Pat. No. 4,642,362.

BACKGROUND OF THE INVENTION

1. Field of the Invention

This invention relates to novel nitrogen-containing oxacalixarene and calixarene derivatives, to polymers including groups related to such derivatives, and to the use of the novel compounds and certain related compounds, particularly for the sequestration of metals, and/or the catalysis of free radical polymerisation of acrylic monomers of the kind described in British Patent Application No. 8700467.

2. Description of the Related Art

U.S. Pat. Nos. 4,556,700 and 4,642,362 Harris et. al. describe certain calixarene derivatives.

McKervey et. al. J. Chem. Soc. Commun. 1985 p.388 describes the cation transfer properties of alkyl calixaryl acetates.

Olmstead et al., J. Am. Chem. Soc., 1985, 107, 8087–8091, describe complexes of p-tert.-Butylcalix[4]arene with the transition metals Titanium (IV), Iron (III) and Cobalt (II).

Izatt et al., J. Am. Chem. Soc., 1985, 107, 63–66 describe cation transport from multiple alkali metal cation mixtures using a liquid membrane system containing a series of calixarene carriers, specifically p-tert.-butylcalix[4]arene, -calix[6(arene, and -calix[8] arene and p.-tert.-pentylcalix[4]arene, -calix[6]arene and -calix[8] arene.

Calestani et al., J. Chem. Soc., Chem. Commun., 1987 p344 describes the diethylacetamide of p.-tert.-butylcalix(4)arene.

European Patent Application No. 87301900.4 Loctite (Ireland Limited describes certain nitrogen-containing calixarene derivatives and their use in sequestering transition metals selectively.

SUMMARY OF THE INVENTION

The present inventors have prepared other nitrogen-containing calixarene derivatives and oxacalixarene derivatives which have the capability of sequestering metals and/or have other useful properties.

The invention provides novel oxacalixarene and calixarene derivatives of the formula:

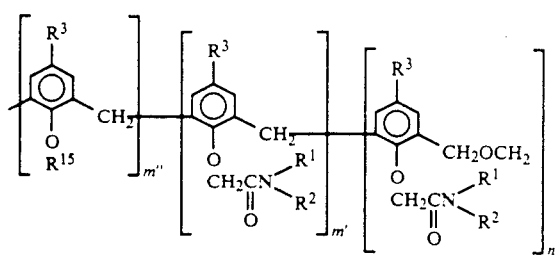

wherein $m' + m'' = 0-8$ $n = 0-8$ $m' \geq \tfrac{1}{2}(m' + m'')$ $3 \leq m' + m'' + n \leq 8$ if $n = 0$, $m' + m'' \geq 4$ $R^3$ is H, halogen, or hydrocarbyl, aryl, hydrocarbylaryl or a substituted derivative thereof and $R^3$ may be the same or different on each aryl group;

$R^1$ and $R^{15}$ which may be the same or different are H or hydrocarbyl, aryl, hydrocarbylaryl or a substituted derivative thereof;

$R^2$ is selected from:

$R^4$ which is H, or hydrocarbyl, aryl, hydrocarbylaryl or a substituted derivative thereof,

wherein $R^5$ and $R^6$ which may be the same or different are H, or hydrocarbyl, aryl, hydrocarbylaryl, or a substituted derivative thereof, —$OR^1$, wherein $R^1$ is as defined above, and $R^{17}$ which is a residue of a hydrocarbyl, aryl, or hydrocarbylaryl group or of a substituted derivative thereof providing a bond to another oxacalixarene or calixarene derivative of formula 1 wherein $R^2$ is $R^{17}$, provided that when $m'' = n = 0$, and $m' = 4$, $R^1$ and $R^2$ are not ethyl groups.

The invention also provides a method of sequestering metals which comprises contacting a metal-containing medium with an oxacalixarene or calixarene derivative of formula I as defined above, but also including the compounds excluded from the above definition by the proviso.

In one aspect, the present invention provides amide-functional oxacalixarene derivatives of formula I above wherein n is at least 1 and $R^2$ is $R^4$. Preferred oxacalixarene derivatives are (i) an oxacalix-4-arene of formula

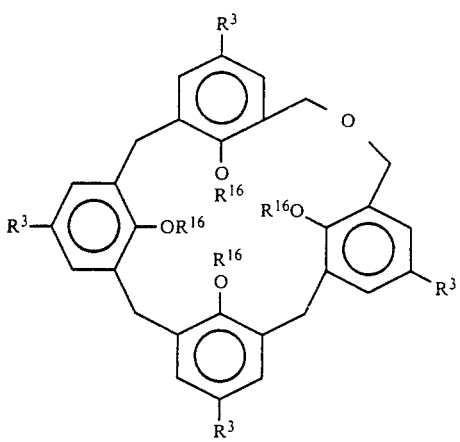

(ii) a dioxacalix-4-arene of formula

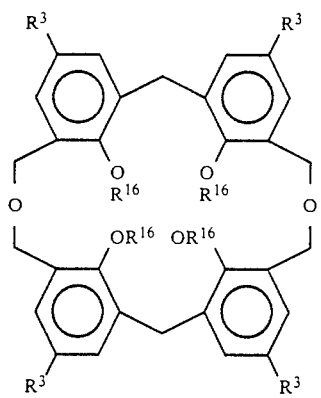

(iii) a trioxcalix-3-arene of formula

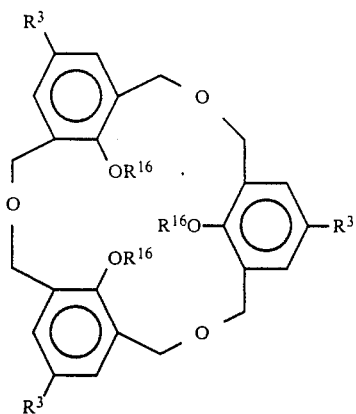

wherein $R^{16}$ is

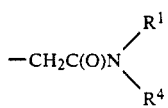

and $R^3$ and $R^4$ ar as defined above.

These amide-functional oxacalixarene derivatives, as well as the amide functional calixarene derivatives of formula I wherein $m''=n=0$ and $R^2$ is $R^4$, have the surprising capability of sequestering transition metals such as copper and silver, transition series elements such as manganese, alkaline earth elements such as calcium and magnesium, and Group III elements such as aluminium in addition to alkali metals.

The amide-functional calixarene derivatives are also effective as polymerisation catalysts particularly in improving the CTV (Cure through volume) performance in an acrylic adhesive applied across a gap, using a metal salt applied to a surface as free radical initiator.

In another aspect the present invention provides oxacalixarene and calixarene hydrazide ester derivatives of formula 1 wherein $R^2$ is

and oxacalixarene and calixarene hydroxamic acid derivatives of formula I wherein $R^2$ is $-OR^1$. These compounds are selective sequestration agents in that they sequester transition metals such as copper but not alkali metals such as sodium.

In a further aspect, the invention provides a polyamide polymer having a plurality of calixarene groups bound thereon, of the formula

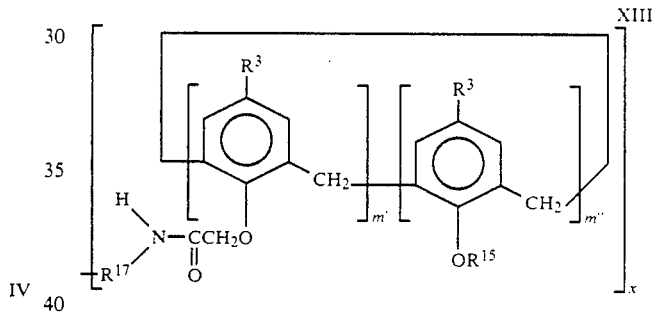

wherein $x>1$, $m' \geq 2$, $m'+m'' \geq 4$ and $R^3$, $R^{15}$, $R^{17}$, are as defined above.

Such a polyamide may be prepared by reacting a calixarene derivative having at least two acid chloride groups with a polyaminoalkane by methods known per se.

In the above compounds of formula I–IV and XIII, the hydrocarbyl groups shall preferably contain from 1 to 10 carbon atoms, more preferably from 1 to 5 carbon atoms and the aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo groups or substituted or interrupted by one or more oxo groups. Halogen may be chlorine, bromine, fluorine or iodine.

The preferred calixarene or oxacalixarene derivatives of formula I are those in which $m''=0$.

The preparation of calixarene derivatives is known and is described, for example, in C. Gutsche et. al. Acc. Chem. Res., 16, 161–170 (1983); in U.S. Pat. No. 4,556,700 Harris et. al., and in J. Inclusion Phenomena 2 199–206 (1984) D. Reidel Publishing Company; the appropriate disclosures of all of which are incorporated herein by reference.

The preparation of aryl calixarene derivatives is described in European Patent Application No. 87306963.7 and equivalent applications in other countries.

Mixed functionality calixarene derivatives are described in European Patent Application No. 0196895 A2 and U.S. Pat. No. 4,642,362 Harris et al. When m" is greater than or equal to 2 in the compounds of formula I, the aryl groups having the —O—$R^{15}$ side chain may be interspersed around the ring between the aryl groups having the —$OCH_2C$ (O) $R^4$ side chain.

In the oxacalixarene derivatives of formula I when (m'+m") and n are greater than 2, the methylene and ether bridges may or may not alternate within the oxacalixarene molecule.

Oxacalixarene compounds may be readily synthesized by methods described in C. Gutsche et al., J. Am. Chem. Soc. 103, 3782 (1981); B. Dhawan et., J. Org. Chem., 48, 1536 (1983) and U.S. Pat. No. 4,098,717 Buriks et al., the appropriate disclosures of which are incorporated herein by reference.

Esterified oxacalixarenes of formula I may be produced by reacting a phenolic oxacalixarene with a halomethyl acetone or a haloalkyl acetate. Potassium iodide may be added to accelerate etherification. This method of production and the etherified oxacalixarenes are the subject of Irish Patent Application No. 153/87 filed 21 Jan. 1987.

Amide-functional calixarenes and oxacalixarenes of formula I may be prepared by methods described in G. Calestani et al., J. Chem. Soc., Chem. Commun., 1987, 344.

DESCRIPTION OF THE PREFERRED EMBODIMENTS

The invention is illustrated in the following Examples:

EXAMPLE 1

Preparation: Acid Hydrazide of p-t-Butylcalix-4-arene 2.48 g of the tetraethyl acetate of p-t-butyl calix-4-arene prepared as in U.S. Pat. No. 4,556,700 by S. Harris et al Loctite (0.0025 mole) was treated with hydrazine mono-hydrate 10 g (0.2 mole) following procedure given in Vogels Textbook of Practical Organic Chemistry 4th Edition revised by B. S. Furniss, A. J. Hannaford, V. Rogers, P. W. G. Smith and A. R. Tatchell, Longman Publishers, London and New York, 1978 page 1125. After gentle reflux for 15 minutes just enough absolute ethanol was added through the condenser to produce a clear solution which was then refluxed for a further 3 hours. After cooling colourless shiny platelets of hydrazine ester were formed which were filtered off—yield 2.5 g (95%)—which were recrystallised from absolute ethanol to give high purity product, m.p.>280° C. characterised by i.r. spectroscopy and elemental analysis as

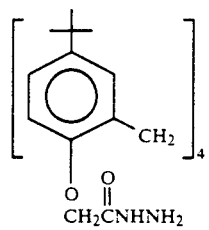

i.r. spectroscopy results=$\nu$3300 (m)NH, 1668 (S) C=O

Elemental Analysis results: (Calc'd) for $C_{52}H_{72}O_8N_8$ C: 11.68, H: 7.76, N: 11.96, O: 13.66; Found C: 65.80, H: 7.61, N: 11.68, O: 13.06).

EXAMPLE 2

Preparation: Diacid Hydrazide of the Diallyl ether of p-t-Butylcali-4-arene 0.73 g of the diallylether of the diethylacetate of p-t-butylcalix-4-arene prepared as in U.S. Pat. No. 4,642,362 by S. Harris et al Loctite (0.0008 mole) was treated with hydrazine monohydrate 1.5 g (0.03 mole) and the same procedure followed as in Example 1 to give 0.7 g (94%) as a colourless solid recrystallised from absolute ethanol to give colourless crystalline product m.p. 242°–5° C. characterised by i.r. spectroscopy and elementary analysis as

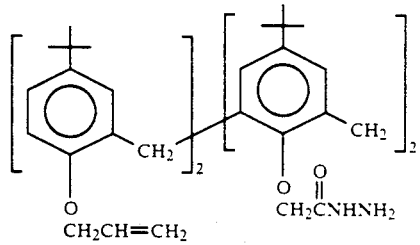

i.r. spectroscopy results=$\nu$3325 (m)NH, 1672 (S) C=O

Elemental Analysis results: (Calc'd for $C_{54}H_{72}O_6N_4$ C: 74.28, H: 8.31, N: 6.42, O: 10.99; Found C: 74.71, H: 8.47, N: 6.44, O: 10.87).

EXAMPLE 3

Preparation and isolation of Cupric picrate-Dihydrazide Calixarene Complex

A 5% methanolic solution of dihydrazide from Example 2 was added to 5% methanolic solution of cupric picrate prepared following a procedure of R. C. Aggarwal and N. K. Singh, Def. Sci. J. 25(4) 1975 p153 to give a pale green precipitate which was washed several times with hot methanol and dried under vacuum to give a pale green solid which was confirmed to be the hydrazide cupric picrate complex by i.r. spectroscopy and elemental analysis. The solid did not melt up to 265° C.

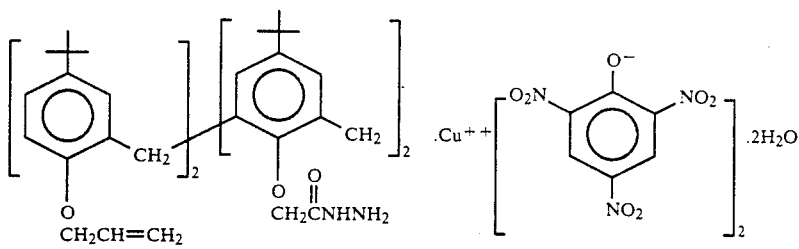

VII

The complex is probably of the following structure:

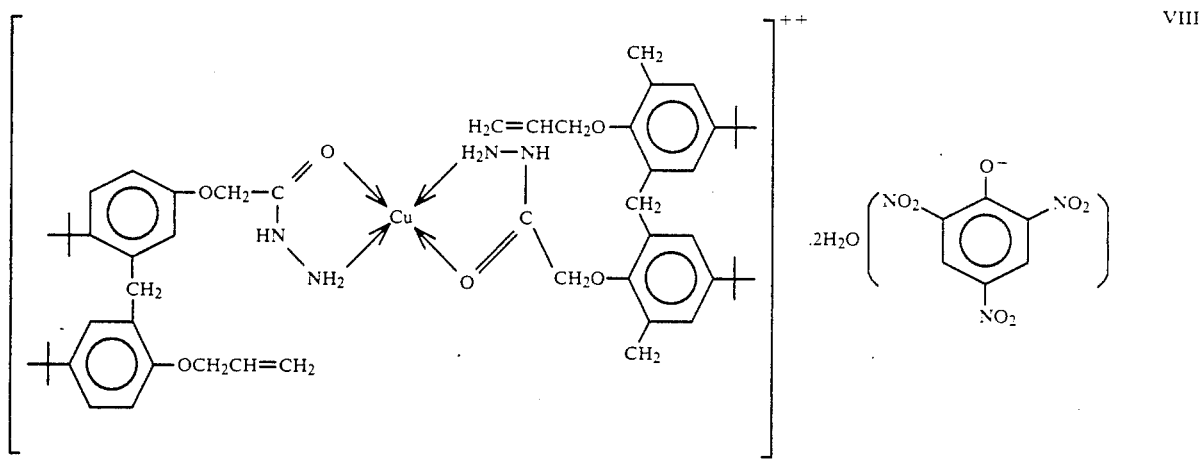

VIII ref. Vol. 2 p1051 in Comprehensive Organic Chemistry, "The synthesis and Reactions of Organic Compounds" by D. Barton and W. D. Ollis. Edited by I. O. Sutherland Pergamon Press.

i.r. spectroscopy results = $\nu$1650 sh(m) 1630 sh(s) 1610(s) C=O, C C

Elemental Analysis results: (Calc'd for $C_{66}H_{80}O_{22}N_{10}Cu$ C: 55.47, H: 5.64, N: 9.80, O: 24.63, Cu: 4.44; Found C: 55.11, H: 5.55, N: 9.60, O: 23.86, Cu 4.56).

EXAMPLE 4

Preparation Hydroxamic Acid Calixarene

To a cooled solution of 1.8 g of the tetraethylacetate of p-t-butylcalix-4-arene prepared by U.S. Pat. No. 4,556,700 S. Harris et al Loctite (0.0073 mole) and 2.02 g (0.029 mole) hydroxylamine hydrochloride in a mixture of 80 mls methanol and 40 mls THF was added a solution of 2.04 g (0.036 mole) KOH in a mixture of 24 ml methanol and 12 ml THF dropwise at −5° C. following a method of A. Liquor in Gaz. Chim. Ital 116 1986 p379. The reaction mixture was then stirred for 5 hrs at −5° C. and then 5 days at room temperature. All volatiles were then removed under vacuum and dilute acetic acid was added to the residue to give 1.5 g product which was recrystallised with dichloromethane to give colourless crystalline shiny platelets product, m.p. 198°–200° C. characterised by i.r. spectroscopy and elemental analysis as

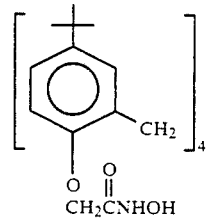

IX i.r. spectroscopy results = $\nu$3230 (m)NH, 1655 (S) C=O

Elemental Analysis results: (Calc'd for $C_{52}H_{68}O_{12}N_4$ C: 66.36, H: 7.28, O: 20.40; Found: C: 64.59, H: 7.57, O: 20.35).

EXAMPLE 5

0.29 g of the ethyl acetate of p-t-butylpseudocalix-4-arene (prepared as in Irish Application 153/87 Loctite (Ireland) Limited which is incorporated herein by reference). (0.00028 mole) was added to 1.1 g of hydrazine hydrate (0.022 mol) and the entire was refluxed for twenty minutes following method of Vogel Practical Organic Chemistry 4th Edition revised by B. S. Furniss, A. J. Hannafor, V. Rogers, P. W. G. Smith and A. R. Tatchell, Longman Publishers, London and New York, 1978 p1125. Then sufficient absolute ethanol was added to give a clear solution after which it was further refluxed overnight, then cooled and the volatiles removed to give 0.23 g colourless solid product (85%). m.p. >280° C. confirmed to be

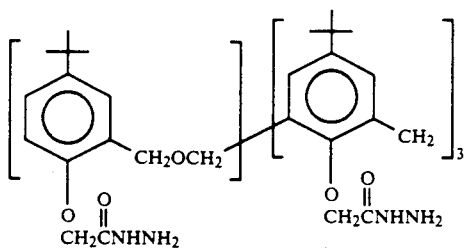

X by i.r. spectroscopy and elemental analysis results:

i.r. spectroscopy results: ν3320 (m)NH, 1673 (S) C=O

Elemental Analysis results: (Calc'd for $C_{53}H_{74}N_8O_9$ C: 65.81, H: 7.71, N: 11.59, O: 14.89; Found C: 64.90, H: 7.09, N: 11.22, O: 14.63).

EXAMPLE 6

Preparation Diethylacetamide of p-t-Butylpseudocalix-4-arene

To 3.84 g p-t-butylpseudocalix-4-arene is also called 7, 13, 19, 25-tetra- tert.butyl-27, 28, 29, 30-tetrahydroxy-2,3-dihomo-3-oxacalix-4-arene prepared following the method of C. D. Gutche, B. Dhawa, K. H. No and R. Mutikrishnan J. Am. Chem. Soc. 103 p3782 1981 from p-t-butylphenol, paraformaldehyde and aqueous potassium hydroxide in refluxing xylene (0.0056 mole) in 25 mls dry DMSO was added 4.50 g (0.030 mole) 2-chloro-N,N-diethylacetamide, 2.6 g (0.022 mole) potassium bromide and 5.60 g (0.041 mole) anhydrous potassium carbonate was stirred under nitrogen at room temperature for 72 hours after which the reaction mixture was poured into 3% sulphuric acid to give an off white precipitate which was washed well with water and dried to give 5.8 g (90%) yield of off white product. Chromatography through neutral alumina using dichloromethane as eluent gave off-white product m.p. 111°–114° C. characterised by infra red spectroscopy and elemental analysis is i.r. spectroscopy results: ν1652 (S) C=O

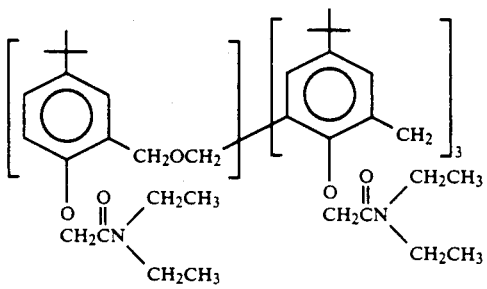

XI

Elemental Analysis results: (Calc'd for $C_{69}H_{102}N_4O_9$ C: 73.24, H: 9.09; Found C: 73.15, H: 8.77)

EXAMPLE 7

Preparation

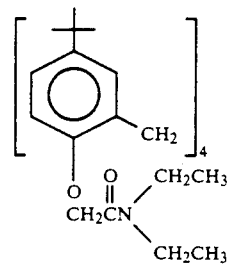

XII

This compound was prepared following the method of G. Calestani et. al. J. Chem. Soc. Chem. Commun. 1987 p344. In the same reference it is reported that this compound sequesters alkali metal ions e.g. sodium. We have made the rather unexpected discovery that this compound also sequesters transition metals such as copper.

Ion extraction by Nitrogen-containing Calixarenes

The ion binding abilities of nitrogen-containing calixarenes were measured by extraction of metal picrates from aqueous into organic media. In each experiment a solution of the nitrogen-containing calixarene in dichloromethane was prepared at $2.5 \times 10^{-4}$M. Silver and cupric picrates were prepared as aqueous $2.5 \times 10^{-4}$M solutions (see Aggarwal et al Def. Sci. J., Vol. 25, October 1975, 153).

A neutral aqueous solution picrate solution was prepared such that the concentration of sodium picrate was $2.5 \times 10^{-4}$M. Equal volumes of each solution (5 milliliters) were shaken together for 3 minutes and the percentage extraction of metal picrate into organic phase was determined by measuring the increase in absorbance of dichloromethane layer at λm ca 355 nm (cupric and silver picrate) and λm 387 nm (sodium picrate) in a u.v. spectrophotometer. The results are presented in the following table.

| Compound | m.p. | % ε Silver Picrate | Cupric Picrate | Sodium Picrate |
|---|---|---|---|---|
| Ex 1 | >280° C. | 5.9 | 30.0 | <1 |
| Ex 2 | 242-5° C. | <1 | 3.8 | <1 |
| Ex 4 | 198-200° C. | <1 | 3.9 | <1 |
| Ex 5 | >280° C. | 6.6 | 31.6 | <1 |
| Ex 6 | 111-4° C. | 48.2 | 10.4 | 57.0 |
| Ex 7 | 230-3° C. | 81.3 | 9.6 | 95.4 |

EXAMPLE 8

To an adhesive formulation based on 16.9% by weight hydroxypropyl methacrylate, 6.1% acrylic acid, 47.1% monomer B (a urethane acrylate prepared by reacting two moles of toluene diisocyanate with one mole of hydrogenated bisphenol A, diluting the reaction mixture with methyl methacrylate and further reacting it with two moles of hydroxyethyl methacrylate in manner disclosed in Example V of U.S. Pat. No. 3,425,988), 23.6% monomer A (a urethane-acrylate reaction product of toluene diisocyanate and the hydroxy polyoxypropylene derivative of trimethylol propane (commercially available under the trademark PLURACOL T P 2450) having unreacted isocyanate functionality capped with hydroxyethyl methacrylate), 1% saccharin, 1% acetylphenyl-hydrazine and 1.9% cumene hydroperoxide was added varying quantities of the compound of Example 7 prepared as described in G. Calestani et al. J. Chem. Soc. Chem. Commun. 1987 p344, m.p. 230°-3° C.

The adhesive composition was stirred until all of the calixarene derivative composition had gone into solution, then treated on grit blasted mild steel lapshears primed one or both sides with brushed-on copper activator, Loctite's 'Primer N'.

The lapshears were at the gaps indicated in the tables below. The composition was cured for 24 hours at room temperatures. The results of the tests shown in the Tables below demonstrate that CTV (cure through volume) performance was improved markedly.

Grit Blasted Mild Steel Lapshears; 24 Hour Test Room Temperature; 0.7 mm Gap; Double Sided Activation with Copper Salt

| Additive | 82° C. Stability | Strength Tensile Shear daNcm$^{-2}$ | |
|---|---|---|---|
| | | 0 mm Gap | 0.77 mm Gap |
| 0 | >2.5 hrs | 289 | 9 |
| 1% Calixarene Derivative | >2.5 hrs | 181 | 16 |
| 5% Calixarene Derivative | >2.5 hrs | 180 | 21 |

EXAMPLE 9

Preliminary Preparation A 1.4 g of the diallyl ether of the diethyl acetate of p-t-butylcalix-4-arene prepared as in U.S. Pat. No. 4,642,362 S. Harris et al (0.00155 mole) was hydrolysed with excess KOH in water/ethanol by refluxing for 48 hours following the method described in European Patent Application 87 301 900.4 Loctite (Ireland) Limited. Acidification with sulphuric acid and water washing of the colourless precipitated solid gave upon drying 0.95 g product as a colourless solid (73%) confirmed by infra red analysis to be the desired diacid product A:

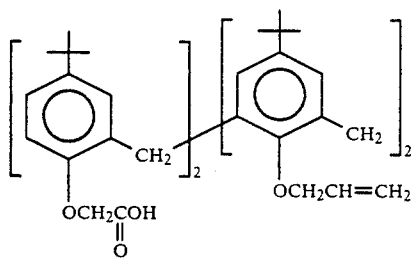

A i.r. spectroscopy results: $\nu$3370 (S) broad-COH, 1735 (S)-(HO)C=O

Preliminary Preparation B 0.95 g (0.0011 mole) of diacid product A was treated with 2.5 g (0.0197 mole) oxalyl chloride in 10 mls dichloromethane under nitrogen with stirring at room temperature following the procedure described in European Patent Application 87 301 900.4 Loctite (Ireland) Limited. Removal of volatiles gave 0.99 g (100%) of buff coloured acid chloride produce which was not further purified in view of its moisture sensitivity. Infra red analysis confirmed its structure to be the diacid chloride B:

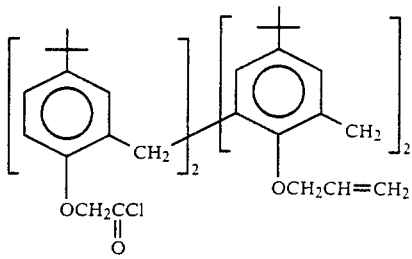

B i.r. spectroscopy results $\nu$b 1810 (S) (Cl) C=O

Preparation of Polymer Bound Calixarene Compound

Following the method of W. R. Sorenson and T. W. Campbell in Preparative Methods of Polymer Chemistry Second Edition Interscience Publishers 1968 p96 the 0.99% of calixarene diacid chloride B (0.00112 mole) in 30 mls of dry 1,2,4-trichlorobenzene (in place of chloroform) was added at room temperature to 0.162 g (0.00112 mole) 1,8-diaminooctane and 0.227 g (0.00224 mole) triethylamine (as acid acceptor) in 40 mls dry 1,2,4-trichlorobenzene under nitrogen with stirring. After 24 hours reaction time the reaction mixture was poured into 1 liter of heptane to give a white precipitate which quickly fell to the bottom. The precipitate was filtered off and washed well with further heptane and dried to give 0.8 g (75%) polyamide calixarene as an off-white solid. The material was further taken up in dichloromethane which was washed well with water to remove amine salts and dried. Following solvent removal, pure off-white solid product was collected which was confirmed by HPLC, infra red and elemental analysis to be polyamide calixarene product.

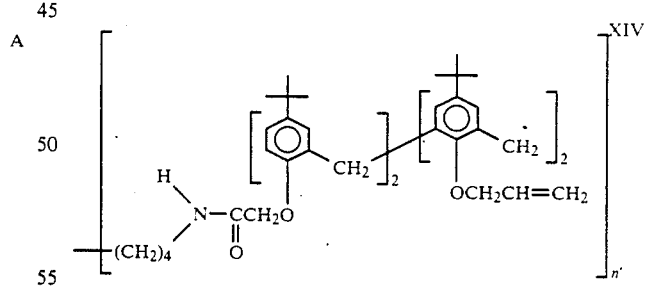

XIV n'=ca 6. The product softened at 168° C. and completely melted by 173° C. H.P.L.C. analysis: Waters Millipore Sugar Analyzer/Liquid Chromatograph; PL gel 10$\mu$; 100 Å, 500 Å, and 1000 Å columns in series; dichloromethane as eluent, 1.2 mls/min; U.V. Detector $\lambda$ m 250 nm; retention volume: 15.2 minutes.

H.P.L.C. Comparison

Polystyrene of 9500 molecular weight as standard: retention volume: 14.3 minutes.

The calixarene derivative of formula C

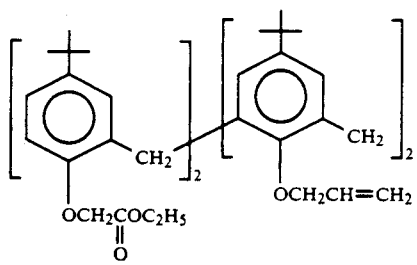

C

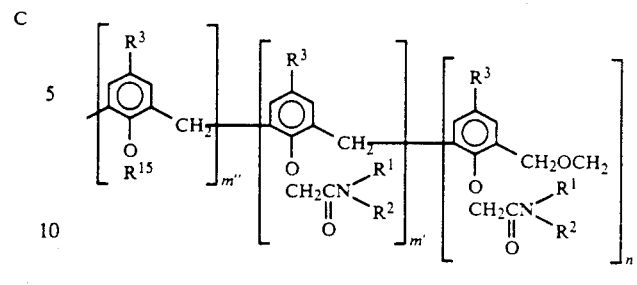

I having a molecular weight of 901; retention volume: 18.5 minutes. If in Formula XIV, n'=1, the molecular weight of the product would be 953.

Based on retention volume time, the molecular weight of the actual product XIV obtained was estimated as approximately 5750. Therefore, n'=6 approximately (6×953=5718).

i.r. results: ν3350 (m) NH, 1653 (S) (NH) C=O

Elemental Analysis results: (Calculated for $C_{62}H_{84}O_6N_2$ C: 78.11, H: 8.88, N: 2.94, found C: 78.88 H: 8.81 N: 2.95).

Ion extraction by Nitrogen-Containing Calixarene

The ion binding ability of the nitrogen-containing calixarene was measured as described above. The results are presented in the following table.

| Compound | m.p. | % ε Silver Picrate | Cupric Picrate | Sodium Picrate |
|---|---|---|---|---|
| Example 9 | 168–173° C. | 9.8 | 10.8 | 6.9 |

As can be clearly seen the polyamide bound calixarene compound sequesters transition and precious metals such as copper and silver as well as alkali metals such as sodium.

This particular example is important because the polyamide calixarene is linear and so is soluble in organic solvents and may therefore be used to provide easy application of a coating to a substrate.

Crosslinked polyamides would have to be prepared on a substrate when in formula XIII m' is greater than 2.

The compounds of Examples 6 and 7 were submitted to further ion extraction tests, using the procedure described above but with picrates of other metals as well as silver, copper and sodium. The results are presented in the following tables:

| Compound | Picrates % ε | | | | |
|---|---|---|---|---|---|
| | Ca | Mg | K | Al | Mn |
| Example 6 | 62.4 | 3.3 | 17.9 | 6.6 | 39.0 |
| Example 7 | 80.9 | 10.0 | 54.0 | 13.1 | 48.6 |

These results illustrate the surprising capability of the nitrogen-containing calixarene and oxacalixarene derivatives to sequester elements in Groups IIa, III and VIIa of the periodic table. The results for calcium and manganese are particularly good.

We claim:

1. Oxacalixarene and calixarene compounds of the formula:

wherein
m'+m''=0–8;
n=0–8;
m'≧½ (m'+m'');
3≦m'+m''+n≦8;
if n=0, m'+m''≧4;
$R^3$ is H, halogen, or hydrocarbyl, aryl, hydrocarbylaryl or a substituted derivative thereof and $R^3$ may be the same or different on each aryl group;
$R^1$ and $R^{15}$ which may be the same or different are H or hydrocarbyl, aryl, hydrocarbylaryl or a substituted derivative thereof;
$R^2$ is selected from:
  $R^4$ which is H, or hydrocarbyl, aryl, hydrocarbylaryl or a substituted derivative thereof,

wherein $R^5$ and $R^6$ which may be the same or different are H, or hydrocarbyl, aryl, hydrocarbylaryl, or a substituted derivative thereof,
—$OR^1$, wherein $R^1$ is as defined above
and $R^{17}$ which is a residue of a hydrocarbyl, aryl, or hydrocarbylaryl group or of a substituted derivative thereof providing a bond to another oxacalixarene or calixarene derivative of formula 1 wherein $R^2$ is $R^{17}$, and said substituted derivatives include those hydrocarbyl, aryl or hydrocarbylaryl moieties substituted with one or more halo groups or substituted or interrupted by one or more oxo groups; provided that when m''=n=0, and m'=4, $R^1$ and $R^2$ are not ethyl groups.

2. Amide-functional oxacalixarene derivatives of formula I as defined in claim 1 wherein n is at least 1 and $R^2$ is $R^4$.

3. Oxacalixarene derivatives according to claim 2 selected from:
(i) an oxacalix-4-arene of formula (ii) a dioxacalix-4-arene of formula

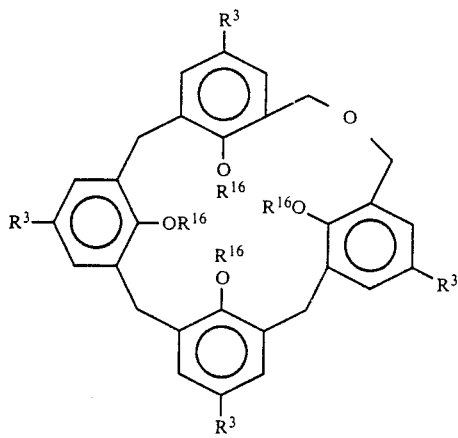

(iii) a trioxacalix-3-arene of formula

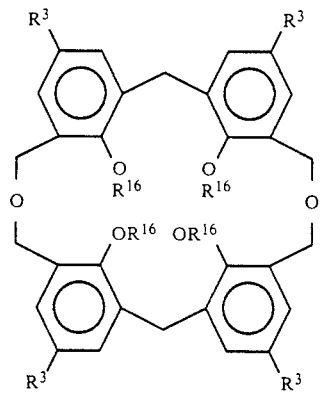

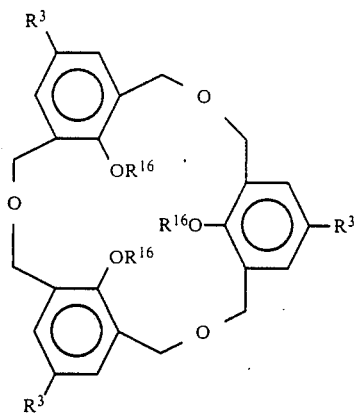

wherein $R^{16}$ is

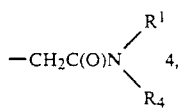

and $R^3$ and $R^4$ are as defined above.

4. Amide functional calixarene derivatives of formula I as defined in claim 1 wherein $m''=n=0$ and $R^2$ is $R^4$.

5. Oxacalixarene and calixarene hydrazide ester derivatives of formula 1 as defined in claim 1 wherein $R^2$ is

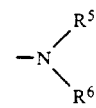

6. Oxacalixarene and calixarene hydroxamic acid derivatives of formula I as defined in claim 1 wherein $R^2$ is $-OR^1$.

7. A polyamide polymer having a plurality of calixarene groups bound thereon, of the formula

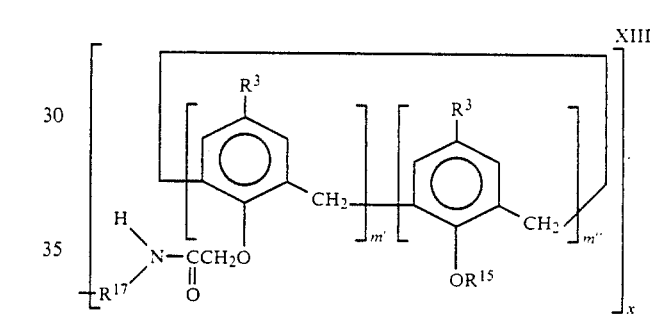

wherein $x > 1$, $m' \geq 2$, $m'+m'' \geq 4$ and $R^3$, $R^{15}$, and $R^{17}$, are as defined in claim 1.

8. Compounds of formula I as defined in claim 1 wherein hydrocarbyl is alkyl or alkenyl having 1 to 10 carbon atoms and aryl has 6-20 carbon atoms.

9. Calixarene and oxacalixarene derivatives of formula I as defined in claim 1 in which $m''=0$.

10. A method of sequestering metals which comprises contacting a metal-containing medium with an oxacalixarene or calixarene derivative of formula Ia:

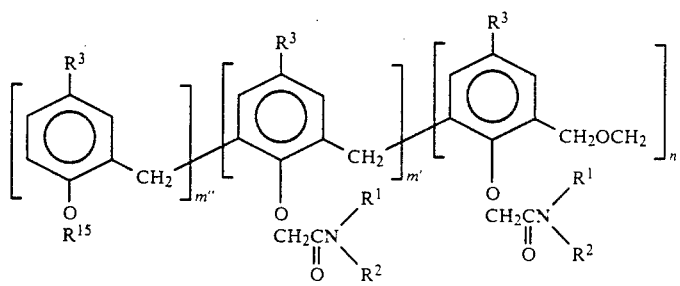

wherein
$m'+m''=0-8$;
$n=0-8$;
$m' \geq \frac{1}{2}(m'+m'')$;

$3 \leq m' + m'' + n \leq 8$;

if $n = 0$, $m' + m'' \geq 4$;

$R^3$ is H, halogen, or hydrocarbyl, aryl, hydrocarbylaryl or a substituted derivative thereof and $R^3$ may be the same or different on each aryl group;

$R^1$ and $R^{15}$ which may be the same or different are H or hydrocarbyl, aryl, hydrocarbylaryl or a substituted derivative thereof;

$R^2$ is selected from:

$R^4$ which is H, or hydrocarbyl, aryl, hydrocarbylaryl or a substituted derivative thereof,

wherein $R^5$ and $R^6$ which may be the same or different are H, or hydrocarbyl, aryl, hydrocarbylaryl, or a substituted derivative thereof, —$OR^1$, wherein $R^1$ is as defined above and $R^{17}$ which is a residue of a hydrocarbyl, aryl, or hydrocarbylaryl group or of a substituted derivative thereof providing a bond to another oxacalixarene or calixarene derivative of formula 1a wherein $R^2$ is $R^{17}$, and said substituted derivatives include those hydrocarbyl, aryl or hydrocarbylaryl moieties substituted with one or more halo groups or substituted or interrupted by one or more oxo groups.

* * * * *

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula I, appearing in [57] ABSTRACT, should be amended to appear as follows:

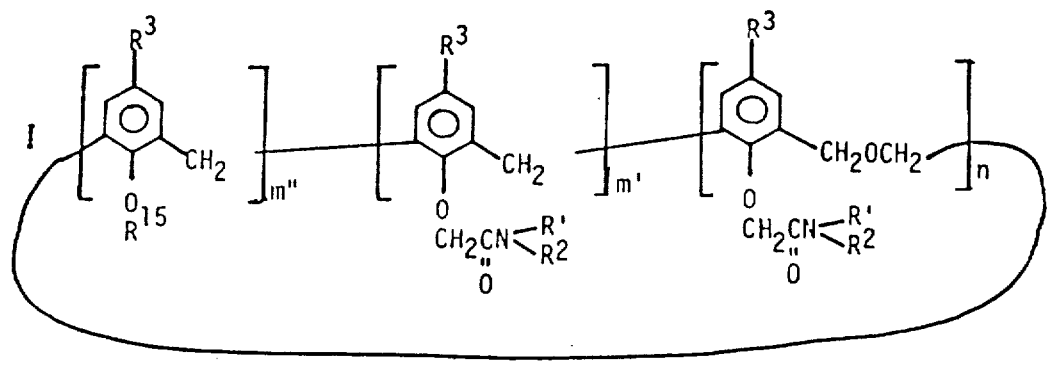

Formula I, appearing in Column 2, lines 1-12, should be amended to appear as follows:

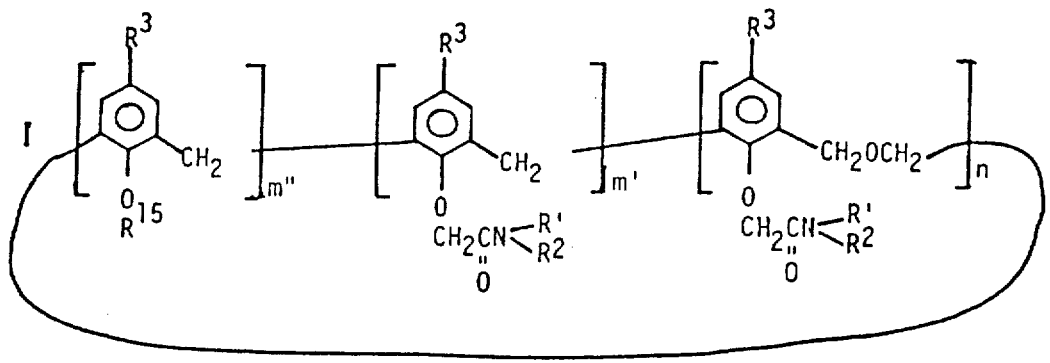

Column 3, line 63, change "ar" following $R^4$ to read --are--.

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula V, appearing in Column 6, lines 1-11, should be amended to appear as follows:

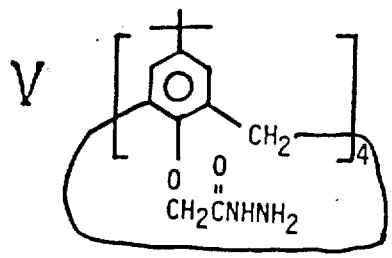

Formula VI, appearing in Column 6, lines 36-44, should be amended to appear as follows:

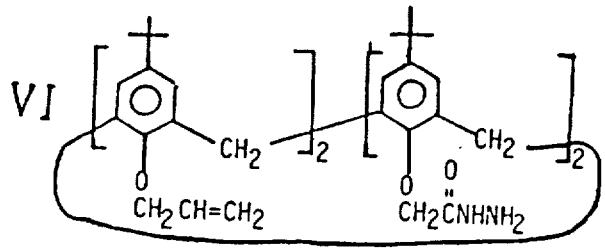

Formula VII, appearing in Column 7, lines 1-12, should be amended to appear as follows:

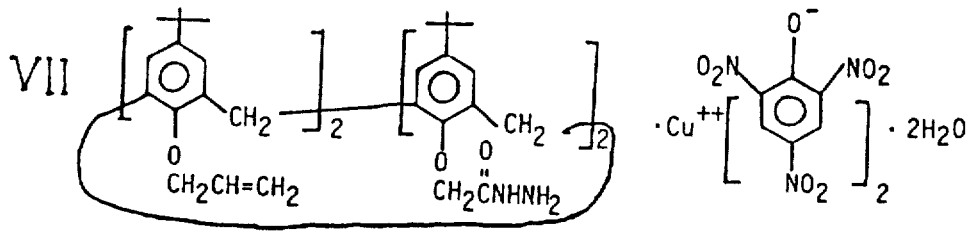

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula VIII, appearing in Column 7, lines 19-35, should be amended to appear as follows:

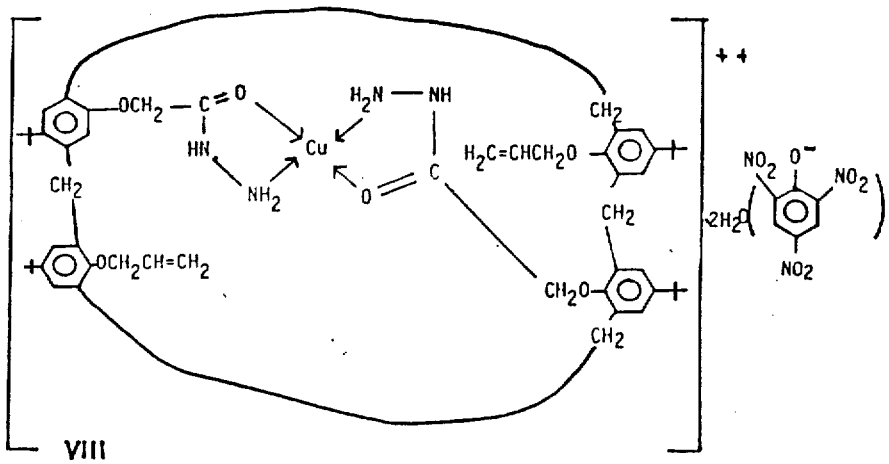

Formula IX, appearing in Column 8, lines 37-46, should be amended to appear as follows:

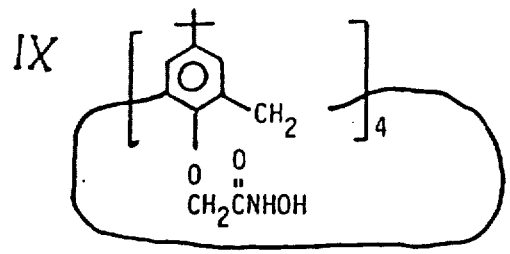

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula X, appearing in Column 9, lines 1-12, should be amended to appear as follows:

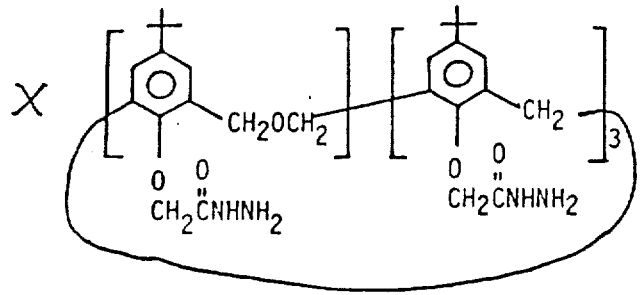

Formula XI, appearing in Column 9, lines 54-65, should be amended to appear as follows:

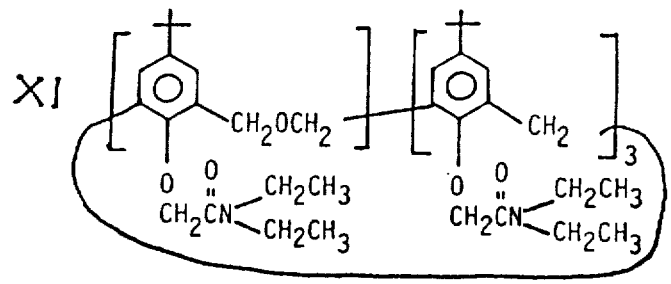

Formula XII, appearing in Column 10, lines 5-15, should be amended to appear as follows:

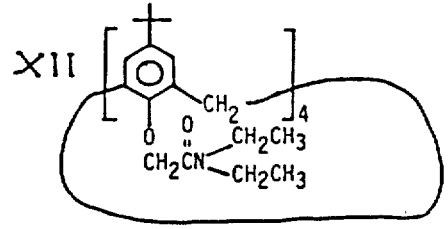

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Product A, appearing in Column 11, lines 45-57, should be amended to appear as follows:

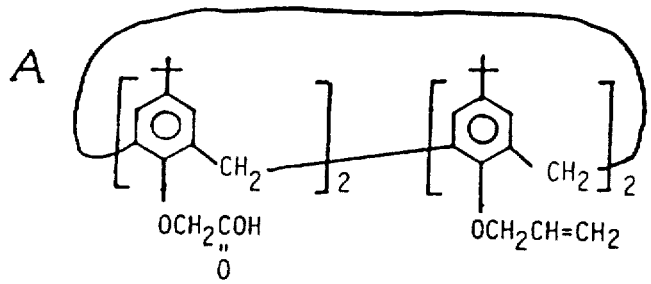

Diacid chloride B, appearing in Column 12, lines 5-16, should be amended to appear as follows:

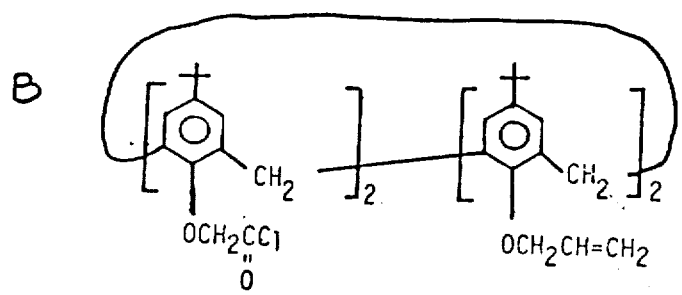

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula XIV, appearing in Column 12, lines 45-55, should be amended to appear as follows:

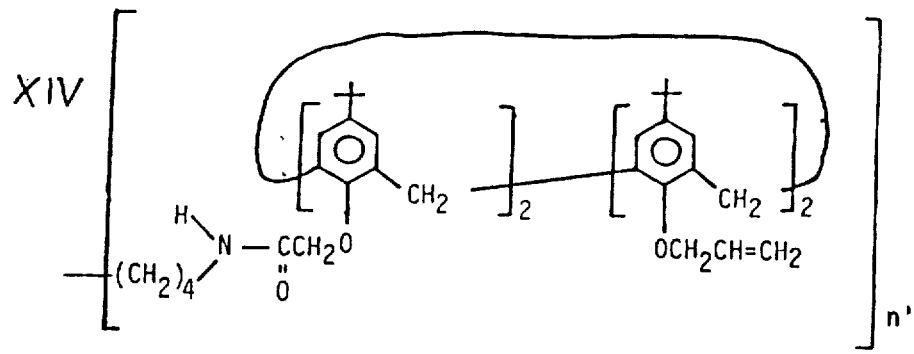

Formula C, appearing in Column 13, lines 1-12, should be amended to appear as follows:

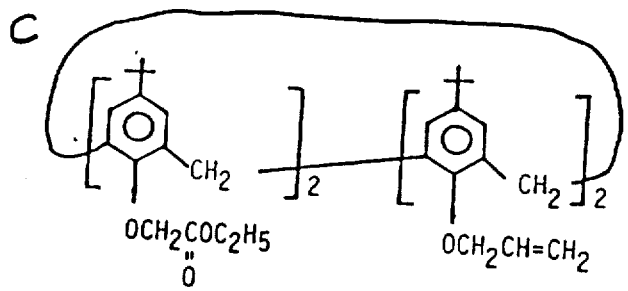

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula I, appearing in Column 14, lines 1-10, should be amended to appear as follows:

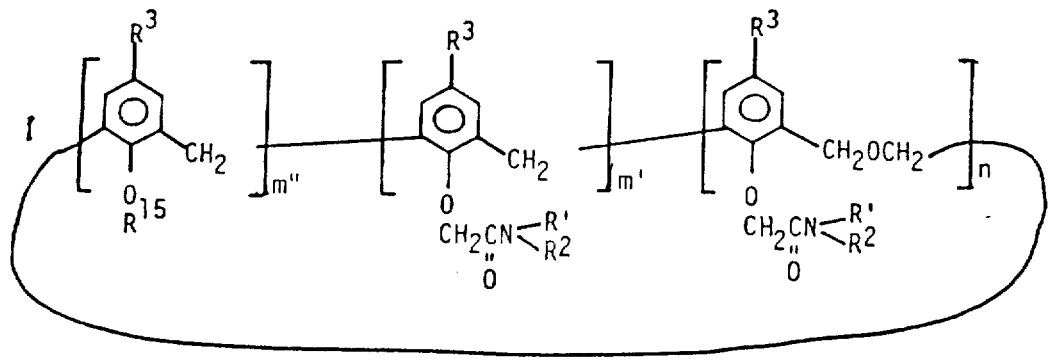

Column 16, lines 2-7, delete: " $--CH_2C(O)N\begin{smallmatrix}R^1\\R_4\end{smallmatrix}$ 4, "

and insert therefor: -- $--CH_2C(O)N\begin{smallmatrix}R^1\\R^4\end{smallmatrix}$ --

UNITED STATES PATENT AND TRADEMARK OFFICE
CERTIFICATE OF CORRECTION

PATENT NO. : 5,043,415
DATED : August 27, 1991
INVENTOR(S) : Stephen J. Harris, et al It is certified that error appears in the above-indentified patent and that said Letters Patent is hereby corrected as shown below:

Formula Ia, appearing in Column 16, lines 50-61, should be amended to appear as follows:

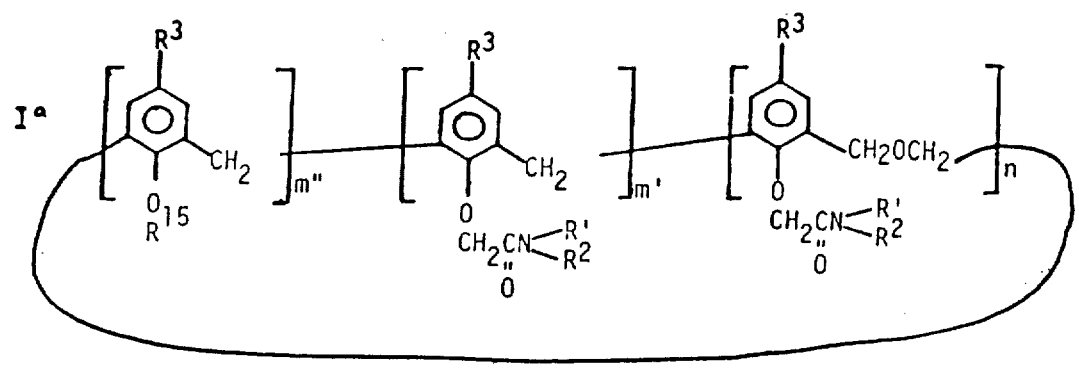

Signed and Sealed this

Fourteenth Day of June, 1994

*Attest:*

BRUCE LEHMAN

*Attesting Officer*       Commissioner of Patents and Trademarks